(12) United States Patent  
Harris

(10) Patent No.: US 7,059,207 B2  
(45) Date of Patent: Jun. 13, 2006

(54) MOTOR DRIVEN SAMPLING APPARATUS FOR MATERIAL COLLECTION

(75) Inventor: Joel Steven Harris, 6073 Valley Field Crescent, Gloucester, Ontario (CA) K1C 5P3

(73) Assignee: Joel Steven Harris, Orleans (CA)

( * ) Notice: Subject to any disclaimer, the term of this patent is extended or adjusted under 35 U.S.C. 154(b) by 116 days.

(21) Appl. No.: 10/673,287

(22) Filed: Sep. 30, 2003

(65) Prior Publication Data

US 2005/0066751 A1 Mar. 31, 2005

(51) Int. Cl.  
*G01N 1/08* (2006.01)

(52) U.S. Cl. .................................................. 73/864.45

(58) Field of Classification Search ..............  
73/864.44–864.45; 175/20, 58; 83/919  
See application file for complete search history.

(56) References Cited

U.S. PATENT DOCUMENTS

| | | | | |
|---|---|---|---|---|
| 2,459,383 A | * | 1/1949 | Levy ........................ | 73/864.45 |
| 3,158,030 A | * | 11/1964 | Cross ................... | 73/864.45 X |
| 4,336,849 A | * | 6/1982 | Hug ..................... | 73/864.45 X |
| 4,606,416 A | * | 8/1986 | Knighton et al. ............. | 175/58 |
| 5,253,720 A | * | 10/1993 | Radford et al. ................ | 175/58 |
| 5,852,875 A | * | 12/1998 | Dolah ........................ | 30/113.1 |
| 6,729,416 B1 | * | 5/2004 | Contreras et al. ............. | 175/20 |
| 2002/0148643 A1 | * | 10/2002 | Contreras et al. ............. | 175/20 |
| 2002/0164272 A1 | * | 11/2002 | Harris ......................... | 422/101 |

FOREIGN PATENT DOCUMENTS

| | | | | |
|---|---|---|---|---|
| JP | 08136418 A | * | 5/1996 | |
| JP | 11117278 A | * | 4/1999 | |

* cited by examiner

*Primary Examiner*—Thomas P. Noland

(57) ABSTRACT

A motorized sample collection apparatus having a hollow clamshell casing with a contoured grip for the fingers, a horizontal extension to eliminate slippage when held in a user's hand, and a flange bottom portion from which a sample sleeve extends downwards. Within the clamshell casing an electric motor is mounted which drives, via spur gears the sample sleeve in a rotational manner. The distal end of the sample sleeve, is a cutting edge circumscribing a circular region. An ejection rod slides reciprocally within the sample sleeve between a retracted stowed position and an expulsion position. User cuts a sample from a substrate by engaging contact between the cutting edge of the sample sleeve and the substrate, applying pressure against the substrate and activating the motor to rotate the sample sleeve. Activation of the ejection rod towards the expulsion position displaces the sample into an appropriate collecting vessel.

15 Claims, 8 Drawing Sheets

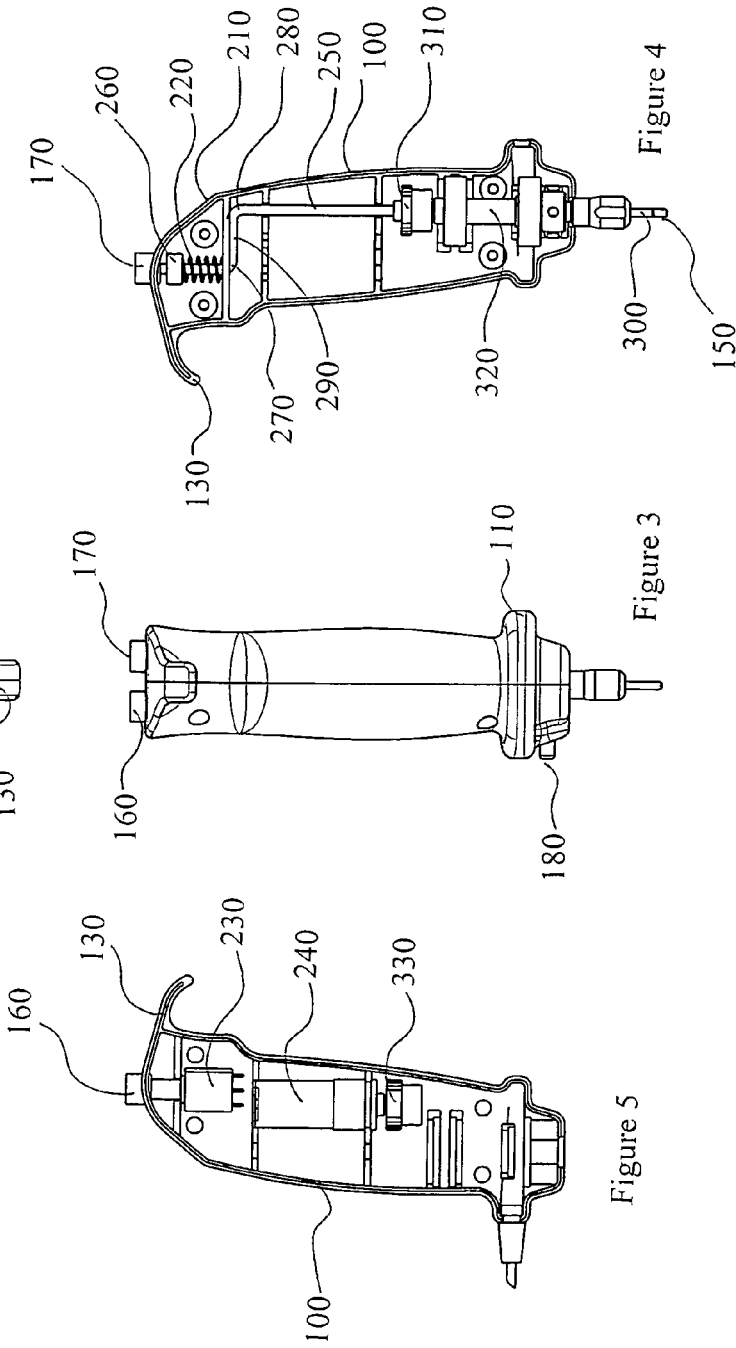

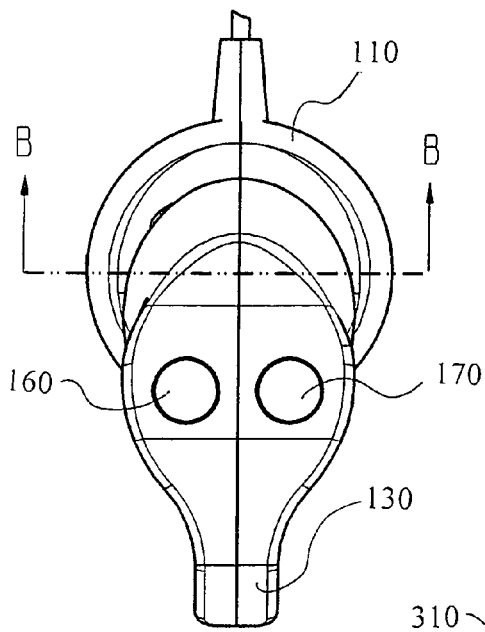
Figure 8
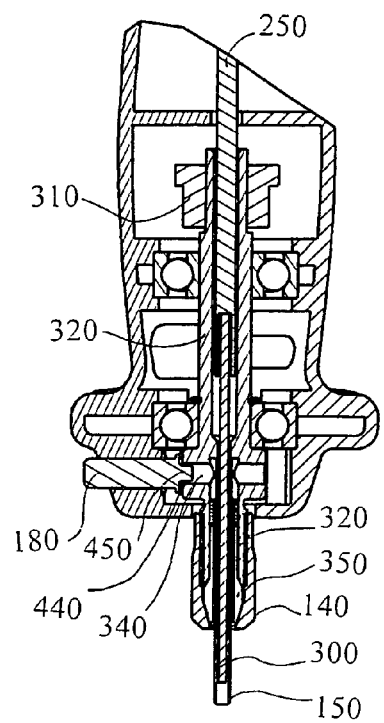
SECTION B-B
Figure 8C
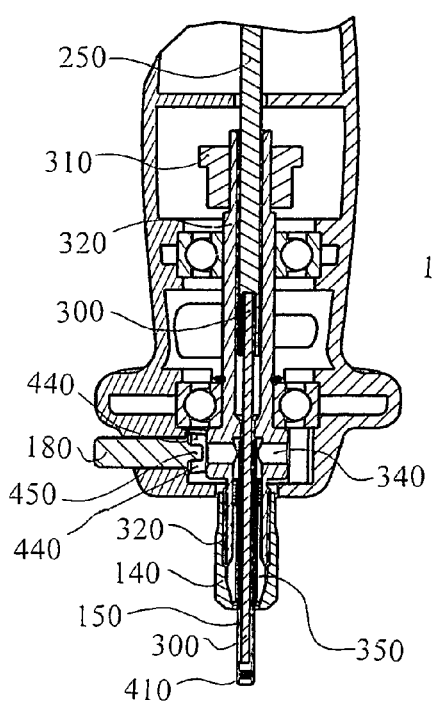
SECTION B-B
Figure 8B
SECTION B-B
Figure 8A

SECTION A-A

MOTOR DRIVEN SAMPLING APPARATUS FOR MATERIAL COLLECTION

BACKGROUND OF THE INVENTION

1. Field of Invention

Micro-sampling devices are conventionally used to slice/cut, scoop, punch or bore samples from source materials such as paper, cloth, wood, gels, human and animal tissues and the like. The samples collected may undergo wet chemical treatment; may be examined microscopically, used to create tissue micro-array slides, or be further chemically analyzed by a variety of analytical equipment including pyrolysis gas chromatographs, mass spectrometers, scanning electron microscopes and Fourier infrared spectrometers.

A widely available and commonly used micro-sampling tool is the garden variety paper punch. These tools are manually operated and available a craft stores or business supply outlets. They have been routinely used to sample dried blood stored on blood cards or for sampling leaves in the study of crop genetic events. There are also dedicated, electric, automated punches, with large footprints designed for high throughput sampling. These systems require the user to manually feed a blood card which, when punched, automatically delivers the sample to an extraction vial, well plate, or other receptacle. These systems are designed for punching dried blood on archival blood cards only.

Paper sampling is used in the neonatal, forensic and genomic markets to analyze blood for a variety of components. Blood samples are collected on filter paper cards and then allowed to dry. A small disc of paper bearing blood is then punched from the card. The blood may then be analyzed for genetic events, diseases, proteins, enzymes or other specific component.

Typically punches are constructed of a punch and die. When operated they create a shearing action thereby tearing the disc of paper from the source card. Writing bond paper is lighter and therefore thinner and a more tightly woven product than filter type papers (i.e. coffee filter papers for example). With lighter bond papers, the shearing action of the punch and die during the punching operation creates little or no artifact fibres. This paper however, does not have the desired absorbent quality required to store blood. Blood samples and other related body fluids (i.e. saliva) are stored on thicker filter paper. This type of paper product is characterized by a loose fibre matrix. Therefore the punch/die shearing operation when punching a sample from such paper will result in the creation of associated artefact fibres. When punching filter paper bearing blood paper fibre artefacts bearing blood will be generated which may be transferred to the next sample punched and into the collection vial receiving the sample. Therefore conventional paper punching systems when used to sample blood cards generate artefacts which may lead to cross contamination.

Bench top, large footprint, automated electric punches have several moving parts both associated with the punching mechanism and the x-y translational stage holding plates or racks of vials below the die. With high throughput these systems generate static. The artefact fiber that are created may be controlled under certain conditions (i.e. de-ionization or other anti-static devices) or the sample may be randomly distributed and not delivered to the desired location. With increased usage static can build quickly and result in artefacts becoming airborne, resulting in carry over and cross contamination. The static may affect delivery of the punched disc down the delivery column resulting in non-delivery, sticking or delivery with a subsequently punched sample doubling up in a single vial.

The racks to receive the samples on the automated punches are positioned below a platen on which the paper sample is positioned for punching. Therefore the operator has no line of sight to confirm that the sample punched has been delivered to the correct vial and whether cross contamination has occurred.

Manual punches, if used for high throughput sampling of blood cards in place of more expensive automated systems, may result in repetitive stress injuries (RSI) over time to the wrist.

This new invention offers a combination of unique features including:

An electric motorized coring operation thereby reducing repetitive stress associated with manual punching and coring devices;

A coring mechanism and not a punch and die punching mechanism, eliminating the creation of paper fibre artifacts and associated cross contamination;

An absence of static build up, a contributing factor to potential cross contamination and carry over of artifacts to other samples or vials;

A completely open line of sight concept insuring sampling of the desired target area and correct delivery to the preferred vial location;

Increased sampling diameters made possible by a plurality of cutting sleeves and can be quickly exchanged;

A simultaneous cutting, lifting and storage of the sample from the source material;

Absence of repetitive stress injury (RSI) associated with manual punches;

Rapid change of sampling tips and tip diameters; and,

Increased throughput without a corresponding increase in the size of the unit.

2. Description of Prior Art

Paper punches such as the Fiskars® crafters punch or other single hole stationary punches are widely available. These punches are inexpensive to purchase, simple to operate and offer a range in punch/die diameters from 1/16th inch to 1/4 inch. The sample may be carefully punched from specific source materials such as paper and the sample delivered directly into the collection well or easily collected after punching with the aid of a tweezers or other forceps, and then inserted into the extraction vial. These manual punches generate little or no static compared with large automated electric punches. However, there are several limitations which make these devices a less than desirable tool for extracting dried blood samples from blood cards.

Paper punches are constructed with the punch and die open and not in contact. This is maintained by a biasing spring mechanism. This allows sample blood cards, within a limited ranges of thicknesses, to be quickly and easily inserted into the punch throat for punching. The area of interest to be punched can be quickly positioned below the base of the punch. The punch may be operated in one hand with the other hand used to hold the source card. This is a suitable method of sample extraction for low sampling programs where the source sample is of suitable thickness and surface dimension.

The punching action for this type of punch occurs when the top and bottom levers are squeezed together in one hand, using the thumb on top and the remaining fingers below. Due to the tension of the spring this operation can create fatigue in the finger, hand and wrist muscles after only a few sample punches are produced, and increase in fatigue over a lengthier period of repetitive punching. Therefore repetitive stress injury may develop quickly with this type of punch where even the smallest sampling pools to be collected become an arduous and painful task.

While the punch and die on this unit remain open at all times allowing for quick insertion of source material for sampling, the vertical height of the throat between the punch and die on these punches may not be large enough to handle some blood cards of greater thickness, or versatile to sample other materials soft enough to be sampled with this instrument but too thick to be inserted.

Another problem with these punches is that the horizontal length of the throat is limited and therefore may restrict sampling over all surface areas and locations of a particular blood card. For example, the Whatman GeneCard requires sampling with a 7.0 mm punch. The description of use states that a sample may be collected almost from the center of the card. Sampling directly from the center of the card is not possible with a conventional paper punch because the horizontal throat of the punch is less than the distance from the edge of the card to the center of the card. Therefore this type of punch is limited to sampling blood cards with surface dimensions that ensures the card can be inserted to allow the punch to reach any location on the surface where the blood may have collected.

These punches use a punch die mechanism and therefore cut samples by shearing a sample from the source material. The punch pushes the sample through the die, essentially tearing rather than cutting the sample disc. This may generate artefact fibres over time with repeated sampling of fibrous blood cards. If the die and surrounding area on the punch is left uncleaned or uncleared between samples, then these artifacts may build up and result in carry over to the next blood card and subsequently be deposited with the next sample into the extraction vial. Therefore this type of punching device lends itself to cross contamination. These types of punches are restricted in their application to primarily sampling blood cards and cannot suitably sample gels, tissue or other soft substrates. These punches have also been used in the agrosciences to study genetic events in crops such as corn, cotton, sunflower and soya plants. The leaf is inserted in the punch throat similar to a blood card. However, with crop studies, sampling from a single leaf may range from 1 to as many as 12 samples. Because plants have a liquid component in the leaves, repeated sampling allows for a build up of plant saps which cause samples to adhere to the punch and are not easily transferred through the die.

The paper punch is a very common, inexpensive sampling tool for sampling dried blood on blood cards and some other flat samples such as leaves.

Another manual paper sampling device, also inexpensive and widely available is the Harris Uni-Core (U.S. Patent Application No. 20020164272). This tool is constructed of a plastic barrel handle, a stainless steel sharpened coring tip and a spring operated ejection actuator. These coring tools are available in inside diameters ranging from 0.50 to 8.00 mm. There is no lever operation and therefore no throat. This allows such tools to sample from any location on a blood card. However, since there is no punch and die mechanism the sample must rest on a pliable support. The stainless steel end of the coring tool is pushed with one hand into the blood card, leaf sample, gel, paint chip, plastic, etc. with slight rotation and gentle downward pressure. The stainless steel tip may also be used to create custom size micro-filters from large samples of filter paper. The sharpened tip passes through the card and into the pliable under support. The cored sample is retained in the tip where it can be later ejected using the actuator.

Because of the razor sharp cutting tip and absence of lever action, repetitive stress on the hand occurs less frequently over the same sampling period when compared with sampling with a craft paper punch. However, the Uni-Core is still not suited for high throughput as repetitive stress injury will develop with prolonged use. The nature of the cutting tip allows this instrument to be used for sampling a variety of materials including gels, paint chips, food, etc., and to create custom size paper filters. This is a versatile sampling tool that can be used on a variety of samples of any surface dimension enabling sampling from any location without restriction in size or thickness.

Both the paper punch and Harris Uni-Core are manual punches and are not designed to punch or core a sample directly into a collection vial, however, the paper punch can accomplish this but not with consistent speed and repetition.

A third example of prior art is from IEM Screening Systems (Division of Fundamental Products Company). This company produces both manually operated and electric automated punching systems. The manually operated system consists of a punch which can hold a specific 96 hole blood card and a plastic 96-hole plate directly below the card. The punch automatically moves each time a sample is punched. Each sample is purportedly punched into a collection well in the plastic micro-titre plate located directly below and in registration with the paper blood card. However, delivery of sample is not visible to the operator and therefore cannot be confirmed after each operation. The sample is manually punched and drops directly into a specific extraction vial. Because of the lever action there is less associated repetitive stress injury than with the former two prior art examples, but RSI can occur with prolonged use. Again a punch and die mechanism is used and this can create artifacts and lead to cross contamination. These punches may only be used with specific cards of a corresponding horizontal surface dimension equal to that of the plate. The sample can only be punched from the center of the printed circle on the card where the blood sample has been entered. If the sample is not centre than the punch head will miss the sample. Therefore this punch mechanism requires sample cards prepared in a specific manner to ensure all samples can be reached for punching. This system is also restricted to sampling 96-spot blood cards and only samples with thicknesses equivalent to blood cards. There are similar restrictions on this sampling tool when compared with the Harris Uni-Core.

These former examples of prior art, while functional, are not suited for high throughput sampling regimes, and, with the exception of the Harris Uni-Core, may only be used with blood cards of a limited surface area and thickness. The Harris Uni-Core may be used on samples of a variety of thicknesses and horizontal surface areas.

Neonatal testing of newborns and paternity testing, as well as other large routine blood sampling programs, have necessitated the development of automated punching systems to handle large volumes of blood cards.

Several automated punching systems are available from BSD Technologies (Australia), EMI (USA), Nanometrics (USA), Biorad (USA) and Wallac (USA), Harris Multi-Punch (Canada). Each of these systems operates on a punch and die mechanism and is designed to punch a single, and sometimes two samples in rapid succession from the same blood card. These systems are only designed to sample blood cards and no other source material.

The sample must be hand fed into the punching region on the automated systems. At this point the punch may be activated with a foot pedal or by pressing a platen upon which the card rests below the punch. Depressing the platen activates the punch.

A plate of uniform footprint but with varying number of holes is positioned below the dye on the punch. After punching, the sample drops down a column into a collection well in the plate. As the next sample is positioned to be punched the plate below the punch/die is automatically moved in the horizontal plane to position the next open well to receive the next punched sample. There are no hopper feeding systems for automated feeding of cards, and therefore each card must be inserted manually. This may create a safety issue as one or both hands may be used and therefore places the operators fingers in the vicinity of the punch. If the operation is not synchronized, the pedal or platen activation may result in operator injury.

The automated punches create static, particularly under dry conditions often encountered during the drier winter months. This may affect delivery of the sample down the delivery column. As well these systems can create artefact fibers due once again to the shearing action of the punch and die which tears the sample. This may result in fibers becoming entangled with samples due to static build up and may lead to cross contamination.

The throat of these units is larger than that for the manual punches, except for the Harris Uni-Core. The thickness may also duplicate that used for paper punches but is not unlimited as is the case with the Harris Uni-Core. These systems offer increased throughput but may not offer the expected confidence that the samples generated are always delivered where expected nor that there is no cross contamination occurring between subsequent samplings. Contamination becomes a chronic condition of these sampling tools which is not always easy to monitor nor are the systems designed to monitor the creation and dispersion of such artifacts.

The new invention combines several features in the prior art. The new invention continues to use the same sharpened coring tip that is used on the Harris Uni-Core. This ensures that a sample from the source material is cut and not sheared or torn, and therefore does not generate artifact contaminant fibres. The new invention is electric and a motor turns the coring tip. This is now a semi-automatic system similar to the electric punching units mentioned in the prior art. However, because there is no punching and therefore fewer moving parts in contact there is little or not static created. Therefore the new invention is electric but does not generate the associated static characteristic of the larger electric automated punching systems. The motorized coring operation eliminates the need to rotate the coring barrel as is required on the Harris Uni-Core. Therefore there is reduced RSI. The unit may be operated in one hand thereby allowing the sample to be positioned with the other hand, similar to the automated systems. However, the new invention is not a punch and therefore the sample is not directed into an unseen collection vial or well. Instead the sample is retained in the coring tip as occurs with the prior art Harris Uni-Core. The sample may now be directed into a well or vial and the operator can visually confirm delivery, which is not possible on the prior art automated punching systems. As the new invention is electric it is designed to allow the operator to process more cards with minimal RSI. As the new invention uses a coring tip and is not restricted by a throat as occurs on stationary paper punches, the new invention may sample any location on samples of unlimited surface size. The tips are disposable and can be easily replaced which is not possible with the prior art manual or automated punching systems. This new invention is designed to further reduce RSI by being contoured to be held in a familiar position in the hand similar to holding an automated/manual pipette (i.e. Eppendorf® pipette) or a video game joystick.

The distal sharpened edge of the tubular cutting sleeve passes through the source material and cuts into the backing support. This operation, in combination with the backing support, forces the extracted sample to be subsequently lodged in the distal end of the tubular cutting sleeve. The sample is then dislodged from temporary storage by forcing it out with an ejection rod.

There are disadvantages with the prior art coring tools, most notably the susceptibility of the operator to Repetitive Stress Injury (RSI) and more specifically Carpal Tunnel Syndrome (CTS), a condition which interferes with the use of the hand and is caused when too much pressure is put on the nerve that runs through the wrist. Even minimal use of the manual coring device over short periods of time has lead to reported wrist discomfort. This discomfort is acerbated when the manual coring device is used in high throughput sampling environments requiring extended daily use by a single operator. The mild, periodic discomfort may lead to more chronic pain such as arthritis. The operation of the manual coring tool requires finger gripping, downward vertical wrist pressure and repeated lateral turning of the wrist in a semi clockwise/counterclockwise direction.

The new invention incorporates the original unique properties of the prior art manual coring tool but has been ergonomically designed to reduce and/or eliminate RSI and CTS. The tubular cutting tip is operated from an electric drive, rotating the tubular cutting sleeve thereby eliminating lateral rotation of the wrist. The wrist does not become fatigued and sore thereby increasing continual use of the instrument. The wrist remains in the preferred neutral straight position when operating the motor driven coring device. Vertical downward motion translation is minimal as the design of this new invention places the cutting edge of the tubular cutting tip in close proximity to the surface of the source material to be sampled. The rotation of the cutting sleeve by the electric motor greatly reduces the required downward pressure, as the sharp edge of the tubular cutting sleeve slices through the source material with minimal contact force. The hollow clamshell handle is vertical and can be held comfortably in either hand. The tubular handle rests in the palm of the hand, and is contoured to accommodate the fingers. There is a thumb rest on the reverse to rest the thumb when not punching or ejecting. At the base of the clamshell handle there is a transverse widening of the body. This allows the base of the hand gripping the instrument to rest on this flange. This hand rest at the base also acts to provide support and protection against the hand slipping into the rotating sample sleeve. The tubular handle is modeled after the familiar joystick design. The wide use of joysticks for extended video gaming has resulted in the evolution of an ergonomic design that minimizes RSI. The rotation of the tubular cutting sleeve is driven by two spur gears juxtaposed within the hollow clamshell. The motor output shaft is mated to a step down spur gear which reduces the speed of rotation of the output shaft. The electric driven tubular cutting sleeve offers the necessary means to conduct high throughput sampling over extended daily periods with minimal or no development of RSI. This high throughput is synonymous with that expected from the electric punch devices discussed earlier. The sharp edge of the tubular cutting sleeve combined with the motor driven rotation of the tubular cutting sleeve reduces the required downward pressure commonly needed and applied when using the manual coring tools. The motor driven cutting sleeve will also allow for cutting of thicker substrate materials without the required downward pressure used with the manual coring tools.

In this new invention, as with the prior art, the sample sleeve serves both as a cutting tool and as a temporary storage receptacle to retain the sample and should be replaced frequently to ensure a sharp edge. The sample ejection system enables quick, safe and clean removal of the sample from the cutting sleeve, either in a rapid action for quick throughput into a collection vial, or more slowly, to position sample on a sampling stage. The electric drive minimizes physical exertion and the contoured surfaces of the clamshell handle are ergonomically designed to fit the hand. The combination of these two characteristics enables the tool to be used in that position for extended periods, with minimal RSI risks. Sample sleeves are held in the drive shaft with a collet system so as to be easily removable for size changes; sterilization or replacement. A single dedicated ejection rod is used in association with a range of different diameter sample sleeves.

This motor driven sampling device was designed for high throughput sampling of dried blood on blood cards or sampling of any other material on media or in situ. Prior art describes a manually operated coring tool which requires finger, hand and wrist movement to core a sample. When used in high throughput sampling regimes this can, and does, lead to repetitive stress injury (RSI). This new electric coring tool has been ergonomically designed to reduce and eliminate RSI from occurring as a result of long term repeated coring operations. The tool rests comfortably in the hand and is gripped by the entire hand encircling the tubular handle. With the finger resting in front, the thumb resting on top and the base of the hand resting on an enlarged rest area at the base, similar to holding a video game joystick.

The hollow tip on this new invention allows for the collection of many samples unlike that of the automated punching system.

Replacement of sample sleeves is realized by a spindle lock mechanism which allows the collet nut to be loosened. The tip slides out and a new tip is inserted. The drive shaft incorporates a shoulder so that the sample sleeves are consistently installed to the same position. The collet nut is finger tightened to lock the tip in position. The ejection rod remains inside the sample sleeve until ejection is required.

A search did not disclose any prior art electric coring tools for sample collecting. One reference refers to a prior patent application for a manual coring tool (Harris). A second patent refers to a battery operated coring tool for coring vegetables and fruits (Dolah).

Canadian Patent Application
2,345,911 Harris
United States
U.S. Pat. No. 5,852,875 Dolah

SUMMARY OF INVENTION

The present invention is an electric sample cutting and collection apparatus comprising a hollow clamshell casing with a contoured grip for the fingers, a horizontal curve extension to eliminate slippage when held in palm, a thumb rest on top and a hand rest at the base of the hollow clamshell casing where a sample sleeve extends downwards from the base. Within the hollow clamshell casing an electric motor is mounted which drives, via spur gears, the sample sleeve in a rotational manner. The end of the sample sleeve, distal from the hand rest, is a cutting edge circumscribing a circular region. An ejection rod slides reciprocally within the sample sleeve between a retracted stowed position and an expulsion position. A user cuts a sample from a source material by engaging contact between the cutting edge of the sample sleeve and the source material, applying pressure against the sample and activating the electric drive to rotate the sample sleeve. The sample cut from the source material becomes lodged within the hollow of the sample sleeve. Actuation of the ejection rod from the retracted and stowed position towards the expulsion position displaces the sample from the hollow of the sample sleeve into an appropriate collecting vessel. The automatic return of the ejection rod is comprised of a compression spring that biases the ejection rod in the retracted and stowed position. Samples may be collected in situ or on a sample substrate. The unit is asymmetric design to be held in either hand like a video game joy stick, with the base of the hand resting on the enlarged flange at the base of the hollow clamshell casing. The grip is grasped in the palm with the front fingers wrapped around the blended contours with the thumb resting on a flat area at the top and to the rear of the hollow clamshell casing. The unit may be operated with either hand. This ergonomic design avoids using the wrist in a bent (flexed), extended, or twisted position for long periods of time. The unit has been sculpted to complement the contours of the human hand, and the design of the apparatus allows the wrist to maintain a neutral (straight) position. The whole hand is used to grasp the handle and can sit on an enlarged hand rest. The thumb also rests on a flat area within easy reach the activation and ejection buttons located at the top. The device is not asymmetrical, thus equally usable in a one-handed manner by either hand.

In this invention, the sample sleeve serves both as a cutting tool and as a temporary storage receptacle to transfer the sample. The sample ejection system enables quick, safe and clean removal of the sample from the sample sleeve. The electric drive eliminates manual exertion by eliminating the need for reciprocating rotary motion of the hand and wrist needed to core a sample from the source material. Eliminating the wrist action in this new invention allows for the operation of the device with the wrist in the neutral or straight position, eliminating stress to the hand. The hollow casing is held by the entire hand and not the fingers, again reducing another contributing source of wrist and hand stress.

This invention may use a plurality of tubular sample sleeves of different diameter so a single sample sleeve is held in the distal end of the apparatus below the hand rest, by a collet system. Below the hand rest is a spindle lock button, to permit tightening and loosening of the collet nut. This collet lock system allows easy removal of the tubular cutting sleeves for cleaning, replacement or size change.

The addition of a motor to rotate the cutting sleeve, together with the ergonomic design of the tool, eliminates repetitive stress related injury resulting from prior art manual coring and punching devices. The electric motor used to rotate the cutting sleeve eliminates the reciprocating rotary action of the wrist required for the Harris Uni-Core. The hollow clamshell casing allows the coring tool to be comfortably gripped in the palm with the fingers wrapped in front and the thumb on top like a video game joystick. This is a design many people are familiar with, given the widespread use of joysticks or manual Eppendorf® pipettes, thereby making this coring design less foreign when initially used and easily accepted to the hand. The positioning of the activation trigger is such that it can be easily reached with either hand, minimizing stress.

The motorized rotation of the sample sleeve and ergonomic design allow for repeated sampling with minimal strain on the hand. It also yields an increased sampling range as the system is capable of sampling a wider variety of source materials of increased thicknesses requiring longer cutting times. The tool is designed to accommodate a specific size range of sample sleeves while using the same ejection rod.

The collet nut, which locks the sample sleeves, can be released by depressing a spindle lock button on the bottom side of the hand rest and turning the collet nut counter-clockwise as viewed from the sample sleeve. The collet nut can be loosened for subsequent removal of the sample sleeves, allowing for cleaning of the sample sleeve ejector rod or replacement of the sample sleeve. The collet nut can be removed to allow access to the collet, which can also be cleaned and replaced as required.

The arrangement and locations of the activation and ejection rod buttons leaves one hand free. This allows the operator to position and hold the source material and acquire a collecting vessel for ejection of sample with one hand, while the other hand operates the apparatus.

This device may be used optionally in conjunction with a substrate upon which the source material is positioned.

The present invention allows the user to portion appropriate size samples from source materials such as food, plants, agricultural materials, gels, clothing, paint chips, film, paper, human or animal tissue and substrates bearing source materials to be sampled such as ink on paper, blood on filter paper, blood on cloth, other biological stains on cloth, etc. This present invention may also be used to create circular micro-filters from large samples of filter paper. Sampling is accomplished by placing the desired source material on the surface of a substrate and penetrating the source material to be sampled with a sharp cutting tool by applying downward pressure, thus the surface of the substrate is also penetrated but not perforated. These and other advantages of the invention will be more particularly realized by a reading of the following detailed description of the invention together with the drawings in which like reference numerals refer to like parts throughout.

BRIEF DESCRIPTION OF THE DRAWINGS

FIG. 2 is an overhead view along the primary axis of the hollow tubular clamshell casing.

FIG. 3 is a projected front view of the apparatus, showing the motor actuation button, ejection button and the collet lock button.

FIG. 4 is a projected side view, with some detail removed for clarity (motor drive assembly), showing the contents of the right hand side of the hollow clamshell casing. It includes the ejection button, compression spring, ejection shaft, plastic spur gears, bearings, collet nut and sample sleeve.

FIG. 5 is a projected side view, with some detail removed for clarity (i.e. ejection assembly), showing the contents of the left hand side of the hollow clamshell casing. It includes the motor actuation button, motor, aluminum spur gear, strain release and power cord.

FIG. 8 is an overhead view along the primary axis B—B of the hollow clamshell casing.

FIG. 8A is a partial view of section B—B in the lower portion of the apparatus showing the ejection rod in the retracted and stowed position.

FIG. 8B is a partial view of section B—B in the lower portion of the apparatus, showing the spindle lock button and the ejection rod in the expulsion position.

FIG. 8C is a partial view of section B—B in the lower portion of the apparatus, showing the spindle lock button engaged in the primary drive shaft.

DESCRIPTION OF PREFERRED EMBODIMENTS

Figure 1:
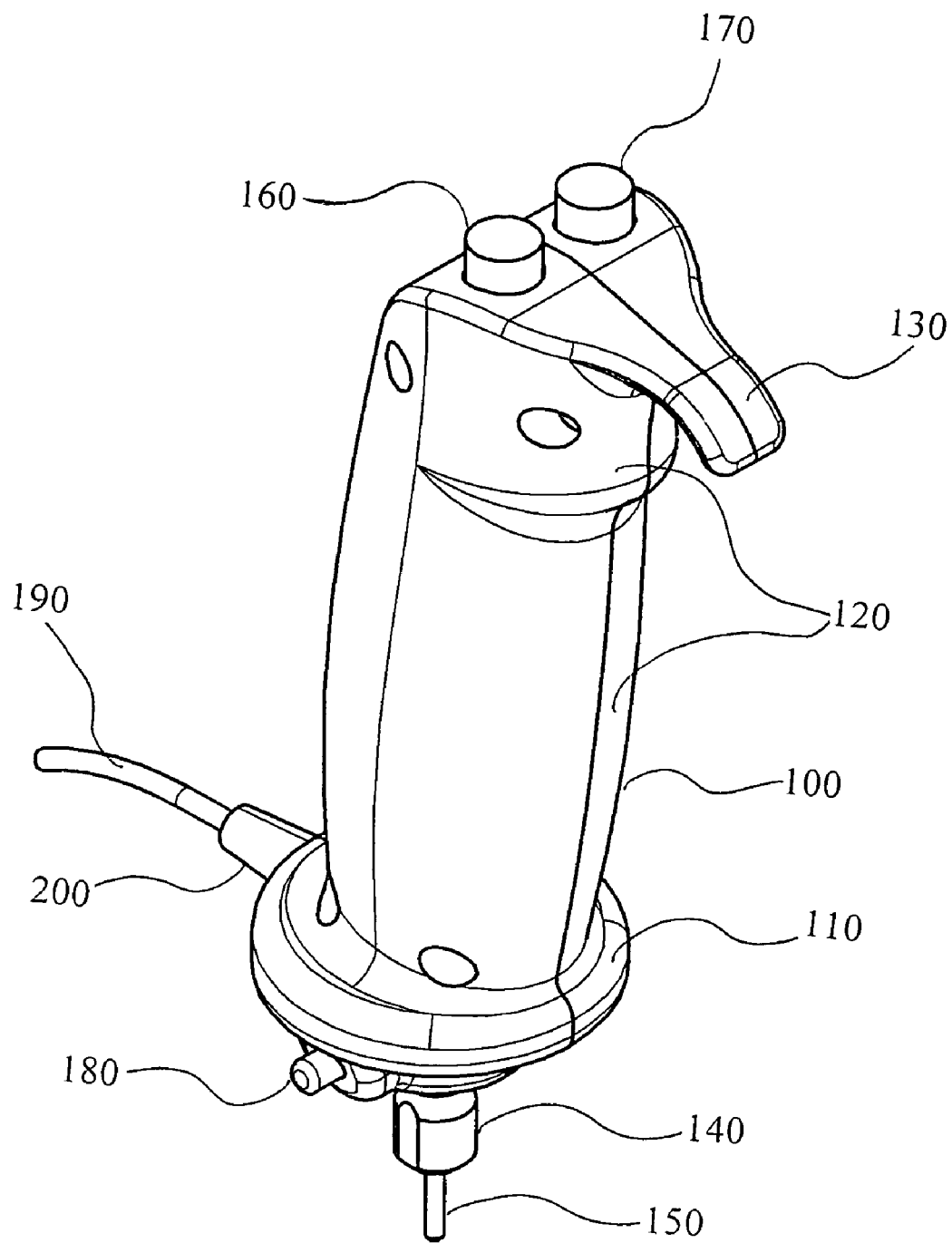
FIG. 1 is an isometric view showing a preferred embodiment of a sample collection apparatus constructed in accordance with the principles of the invention, with the spindle lock button to allow the tightening and release of the collet nut, the motor actuator button, the ejection button, the hand rest at the base of the grip, finger contours at the top and to the front of the grip and a curved finger hook extending in the front and above the finger contours.

Referring to FIG. 1, a preferred embodiment of a sample collection device constructed in accordance with the principles of the invention is shown. A handle feature 100 blends to a horizontal flange feature 110 at the bottom as a hollow clamshell casing. A collet nut 140 at the lower end below the flange 110 holds the sample sleeve 150. To facilitate ease of holding the unit, finger contours 120 are included on the front of the casing. To reduce slipping of the hollow clamshell handle 100 through the hand a curved extension shaped as a hook 130 has also been added as a blended feature above the finger contours 120. The motor actuation button 160 and the ejection button 170 are positioned at the top of the hollow clamshell casing 100. The spindle lock button 180 extends just below the base of flange 110. The power supply cord 190 extends from a cord strain release 200 which extends from the rim of the flange 110.

Figure 1A:
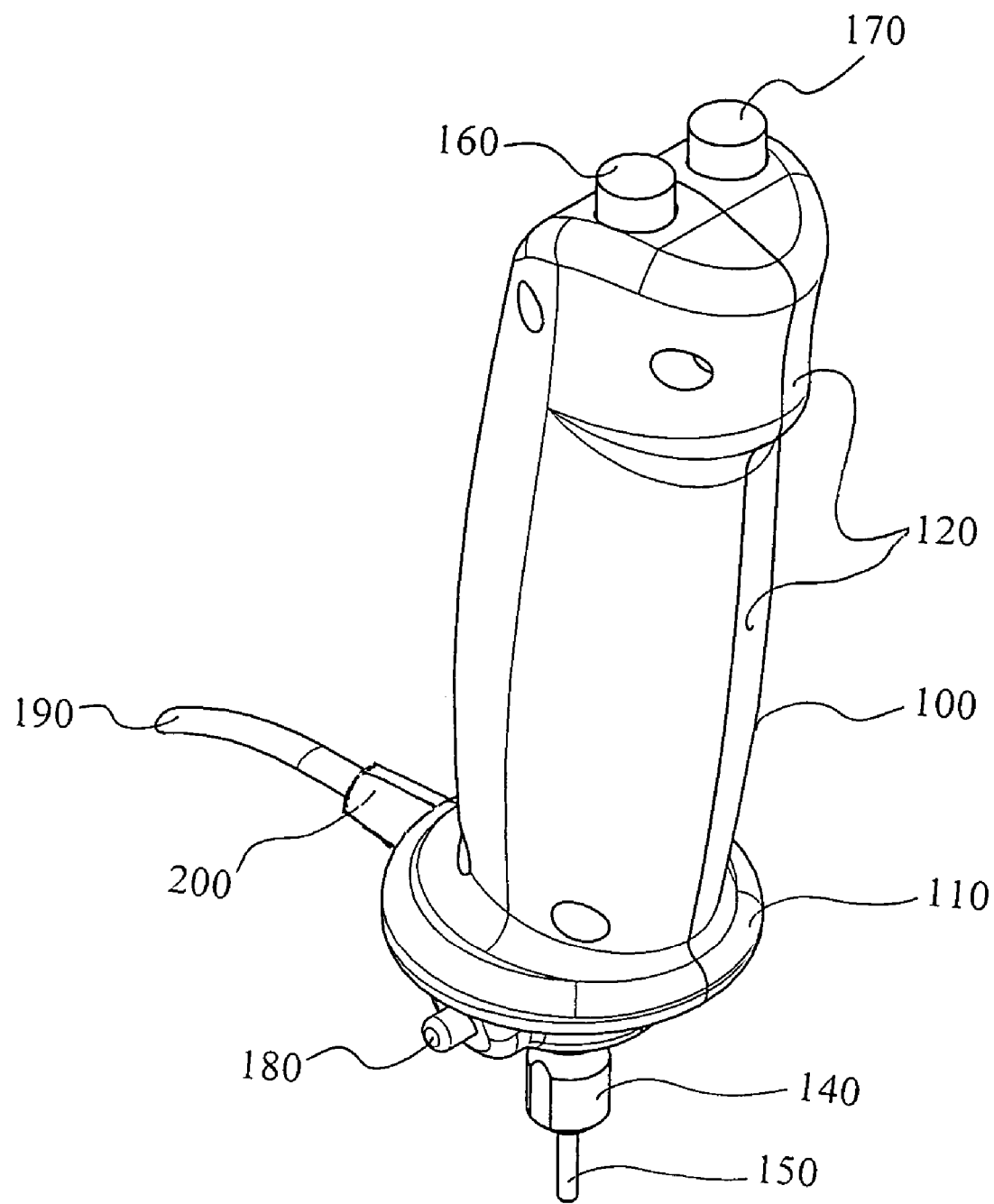
FIG. 1A is an isometric view showing a preferred embodiment of a sample collection apparatus constructed in accordance with the principles of the invention, with the spindle lock button to allow the tightening and release of the collet nut, the motor actuator button, the ejection button, the hand rest at the base of the grip and finger contours at the top and to the front of the grip.

FIG. 1A repeats the embodiments described for FIG. 1 but does not include the blended horizontal extension 130 from the front and at the top of the apparatus which reduces slippage but may not be always a desired feature. All components described in FIGS. 2 to 10 for the invention with the blended finger hook extension are present in the same invention without this blended extension and have not been shown.

FIGS. 2 and 3 repeat the preferred embodiments described for FIG. 1 but are an overhead view and a projected front view of the hollow clamshell casing 100 showing the motor actuation button control 160, ejection button 170 and spindle lock button 180 just under the flange 110. Spindle lock button 180 is hidden under the flange 110 in FIG. 2 and cannot be seen.

FIG. 4 shows a projected side view of the apparatus in which the thumb rest 210 can be better realized at the upper end of the hollow clamshell casing 100. The ejection button 170 is biased in the retracted and stowed position by a compression coil spring 220. The ejection rod 300 is recessed in sample sleeve 150. Thumb rest 210 is positioned below, and on an angle from the motor actuation button 160 and ejection button 170. A push button, normally open, momentary switch 230, which activates the gear motor 240, is positioned below the motor actuation button 160 (see FIG. 5). The ejection button 170, located at the top of the top of the vertical blended boss on the hollow clamshell casing 100, is attached to an ejection shaft 250. The ejection shaft 250 is attached to shaft collar 260 which is biased by spring 210, shown in the stowed position. Ejection shaft 250 includes 2 opposing co-planar 90° bends 270 and 280, separated by a short horizontal span 290 to axial align the ejection rod 300 with the sample sleeve 150. The ejection shaft 250 passes through plastic spur gear 310 terminating within primary drive shaft 320. The ejection rod 300 is pressure fitted into the ejection shaft 250 within primary drive shaft 320 (see FIGS. 8A to 8C). Gear motor 240 has an aluminum spur gear 330 (see FIG. 5) meshing with plastic spur gear 310.

FIG. 5 repeats the preferred embodiments described in FIGS. 1 to 4 and is a projected side view of the hollow clamshell casing 100. When motor actuation button 160 is depressed it activates the push button switch 230 to start gear motor 240, which drives aluminum spur gear 330 which meshes with plastic spur gear 310 and turns sample sleeve 150. When ejection button 170 is depressed it compresses spring 220 and causes ejection shaft 250 with attached ejection rod 300 to travel from retracted position to expulsion position. When spindle lock button 180 is depressed it protrudes into through-hole 340 in primary shaft 320 preventing rotation of the primary drive shaft 320 (See FIG. 6). This enables tightening and loosening of the collet nut 140 for releasing the sample sleeve 150 for cleaning or size change. Sample sleeves 150 within a plurality of diameters can be matched to the various collets 350 that fit the primary drive shaft 320 (See FIGS. 8A and 8C)

Figure 6:
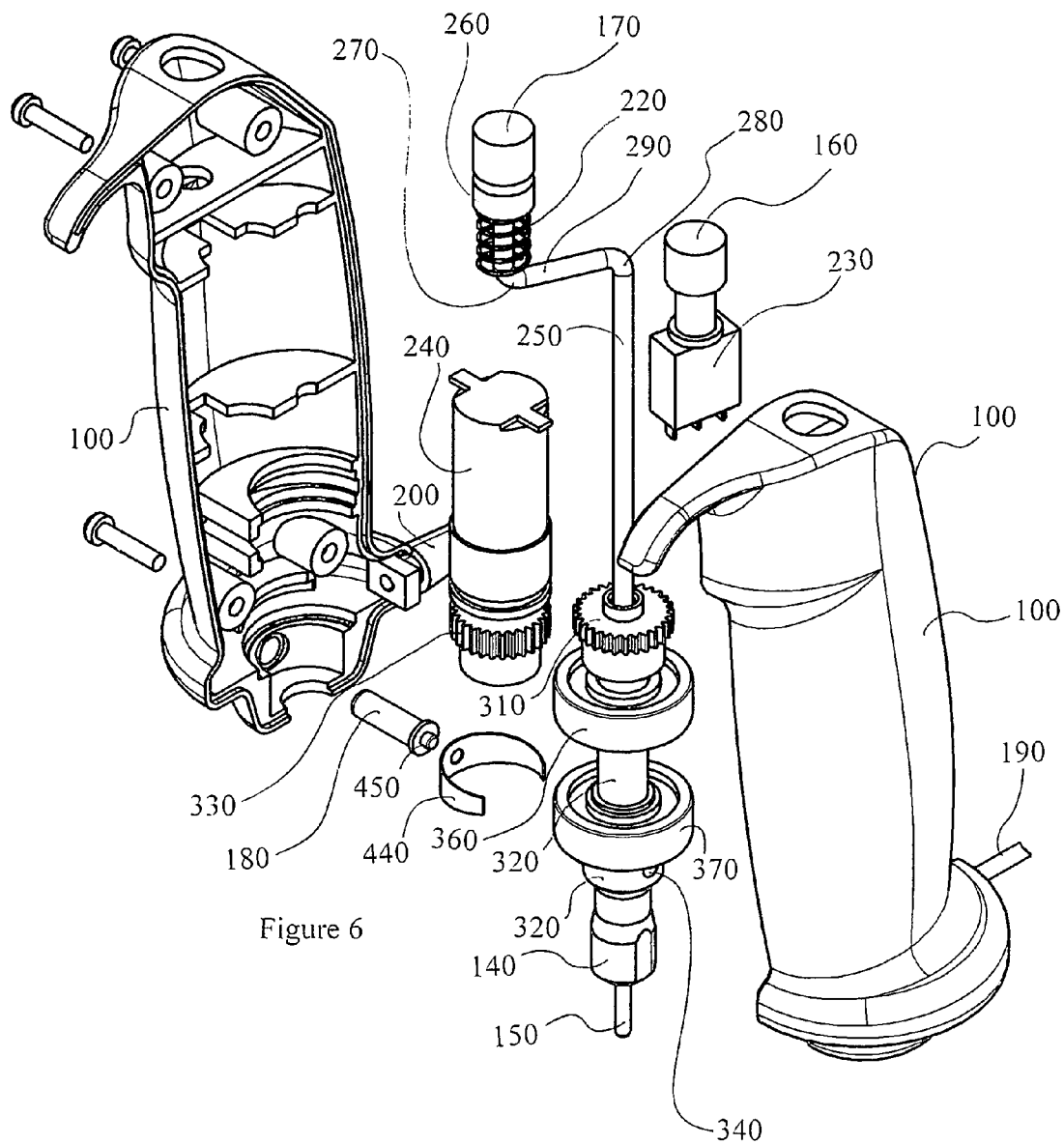
FIG. 6 is an exploded view of the apparatus, showing the details of the sub-assemblies in the apparatus.

FIG. 6 is an exploded view with both sides of the clamshell casing 100 moved to reveal the drive sub-assembly. Electrical power is provided to a low voltage gear motor 240 from power cord 190 via the push button switch 230. An aluminum spur gear 330 is attached to the output shaft 370 (within gear motor 240 and not shown) of the gear motor 240 in position to mesh with another plastic spur gear 310 on the primary drive shaft 320. The use and configuration of standard spur gears 310 and 330 in this embodiment enables the hollow clamshell casing 100 to be in an ergonomically suitable configuration for the hand to hold above the source sample material 380 (see FIG. 7). The primary drive shaft 320 is located between two bearings 360 (upper) and 370 (lower). The upper bearing 360 is used to maintain correct radial alignment of spur gears 310 and 330 and the lower bearing 370 is positioned to suit the axial forces expected during sample cutting. The lower end 390 (see FIGS. 8A to 8C) of the primary drive shaft 320 is threaded to attach the collet nut 140 that compresses the collet 350, which holds the sample sleeve 150. The spindle lock mechanism showing the spindle lock button 180, which is biased in the stowed position by a leaf spring 440. When the spindle lock button 180 is depressed, the cylindrical face 450 on the spindle lock button 180 travels to the through the hole in leaf spring 440 and further into through-hole 340 in primary shaft 320 preventing rotation of the primary drive shaft 320.

Figure 7:
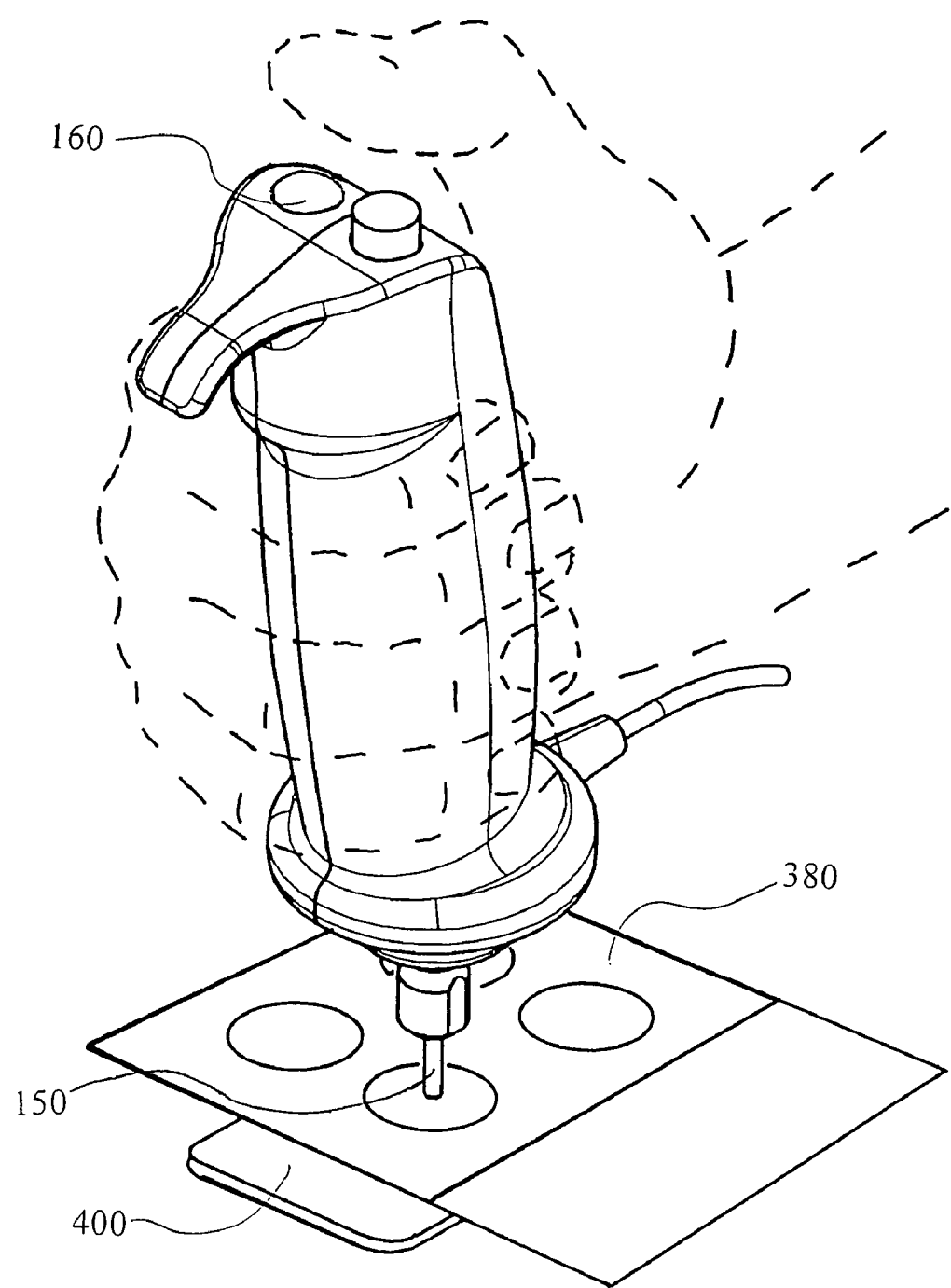
FIG. 7 is an isometric view of the apparatus held in the right hand in the operation of extracting a sample from a source material resting on a substrate. The thumb operates the motor actuation button and the ejection button. This view shows a preferred embodiment of a sample collection apparatus constructed in accordance with the principles of the invention, with the collet nut, the motor actuator button, the ejection button, the hand rest at the base of the grip, finger contours at the top and to the front of the grip and a curved finger hook extending in the front and above the finger contours.

FIG. 7 is an isometric view of the apparatus held in the right hand, showing the sample sleeve 150 above a sample material 380 to be sampled. Source sample material 380 rests on top of substrate 400. The motor actuation button 160 is depressed to activate the motor 240, which drives the sample sleeve 150. Gentle downward pressure is applied and a sample is cored from the source sample material 380. A sample 410, having been cut as described above, is shown ejected beyond sample sleeve 150 into sample collection receptacle 420 (See FIG. 10).

FIG. 8 is a top view of the apparatus, looking along the axis B—B of the sample sleeve 150. FIG. 8A is a detailed section view of FIG. 8 showing the internal sub-assemblies in the retracted and stowed position. The spindle lock mechanism showing the spindle lock button 180 biased to a stowed position by a leaf spring 440 and with the ejection shaft 250 and ejection rod 300 in the retracted stowed position. A sample 410, having been cut as described above, is shown temporarily lodge in the end of the sample sleeve 150.

FIG. 8B is a detailed section view of FIG. 8 showing the internal sub-assemblies in the expulsion position. The ejection system is shown in the expulsion position with a compressed spring 220 biasing the ejection shaft 250 and ejection rod 300 towards the expulsion position.

FIG. 8C is a detailed section view of FIG. 8 showing the internal sub-assemblies in the locked spindle position. When spindle lock button 180 is depressed, the cylindrical nose 450 at the distal end of the button cylinder extends into a through-hole 340 in the primary drive shaft 320. This effectively prevents the primary drive shaft 320 from rotating while the collet nut 140 is loosened or tightened as described above.

Figure 9:
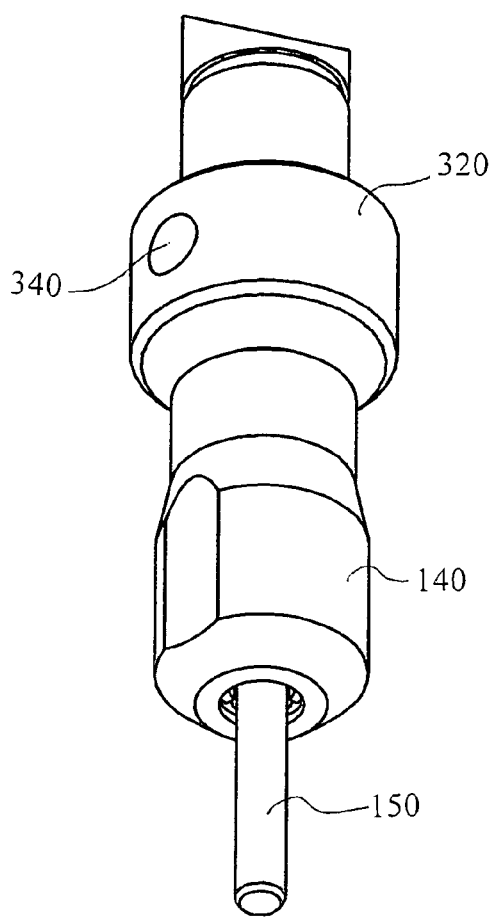
FIG. 9 is an isometric detail view of the sample sleeve and collet system of the apparatus.

FIG. 9 is an isometric detail view of the sample sleeve clamping system showing the primary drive shaft 320 with the through hole 340 for the cylindrical nose 450 on the spindle lock button 180 and collet nut 140.

Figure 9B:
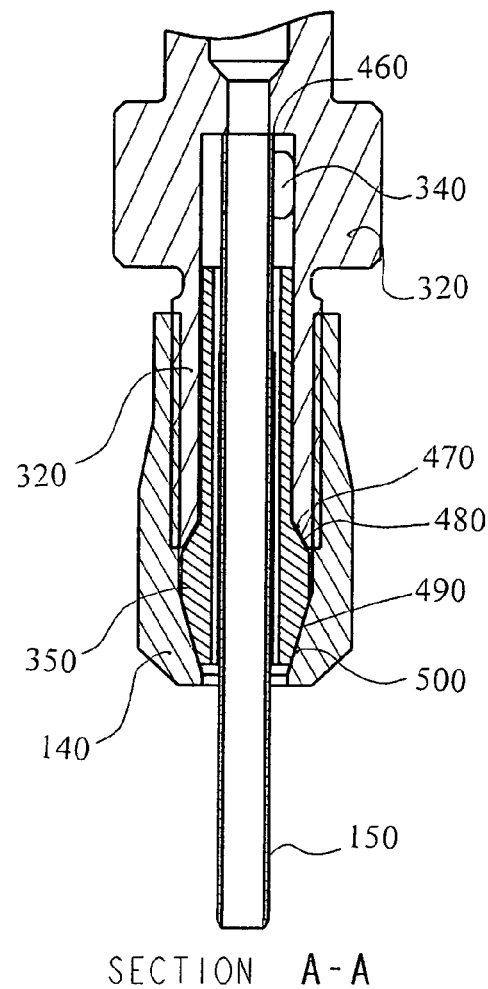
FIG. 9B is a projected section view of the sample sleeve clamping system of the apparatus along the axis A—A of the sample sleeve, showing the primary drive shaft, collet nut, collet, and sample sleeve.
Figure 9A:
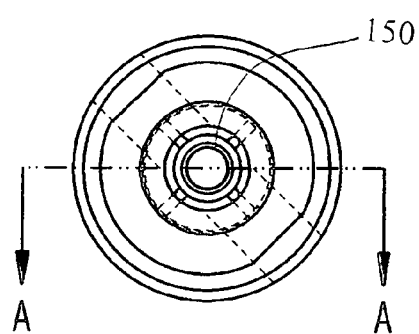
FIG. 9A is a partial detailed view of the apparatus along the axis A—A of the sample sleeve, as seen from the bottom.

FIG. 9A is a bottom view, looking up along the axis A—A of the sample sleeve 150.

FIG. 9B is a projected section view of the sample sleeve clamping system, showing the primary drive shaft 320, collet nut 140, collet 350 and sample sleeve 150. The sample sleeve 150 is inserted through collet 350 to a fixed depth in the primary drive shaft 320, defined by a shoulder 460. The collet 350 has two conical surfaces where the upper face 470 contacts a corresponding internal conical face 480 on the primary drive shaft 320. Similarly the lower conical face 490 on the collet 350 contacts a corresponding internal conical surface 500 of the collet nut 140. When the collet nut 140 is tightened, the collet 350 contracts and clamps the sample sleeve 150 in place, preventing axial or rotational slipping. To release or tighten the collet nut 140 it is necessary to lock the primary drive shaft by depressing the collet lock button 180 and biasing the cylindrical face 450 on the spindle lock button 180 into the through hole 340 on the primary drive shaft 320. Various collets may be provided to suit a plurality of different diameters of sampling cutting sleeves.

Figure 10:
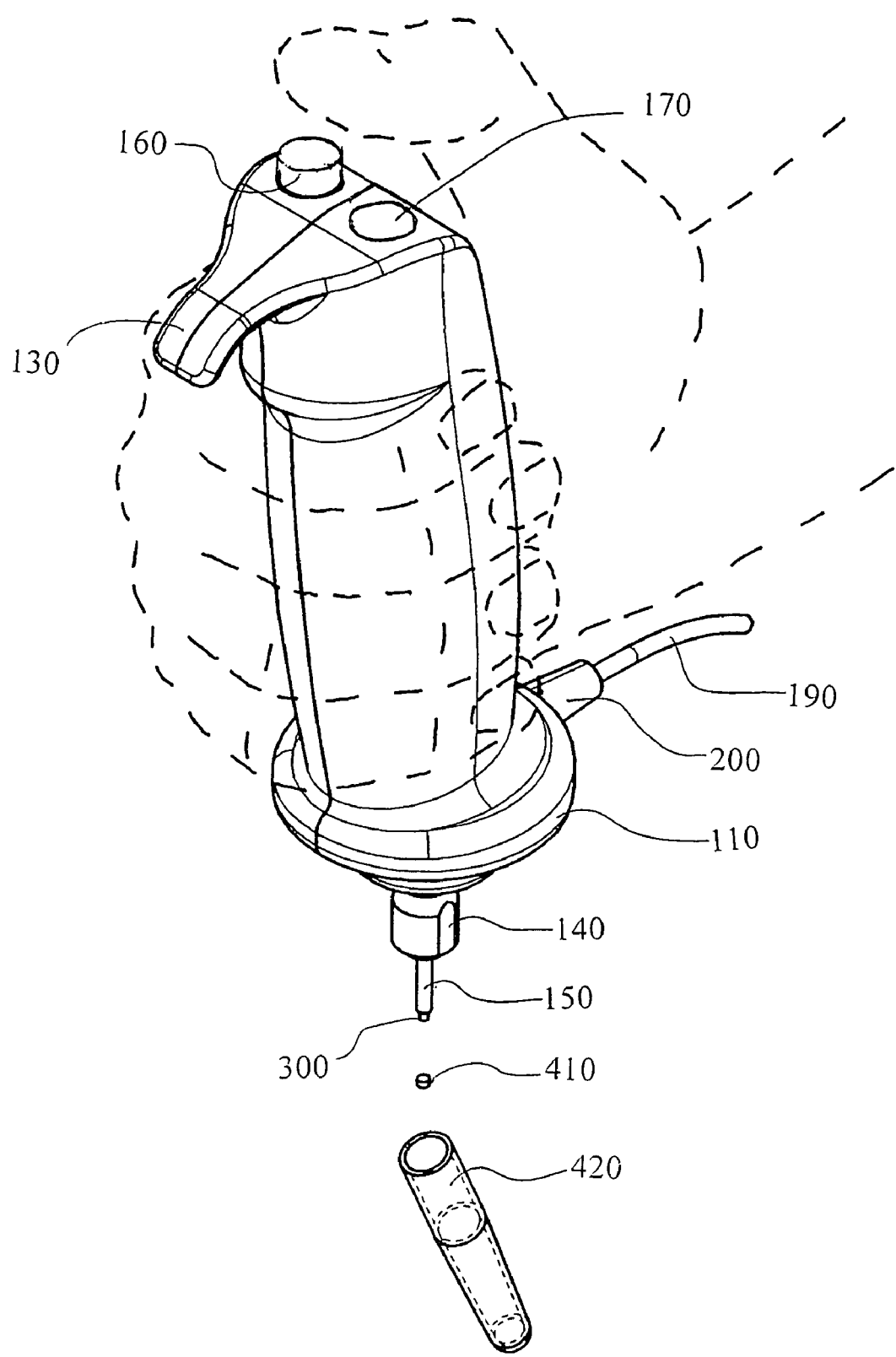
FIG. 10 is an isometric view of the apparatus held in the right hand with the sample sleeve above a receptacle. The thumb depresses the ejection button, expelling the sample in the desired location.

FIG. 10 is an isometric view of the apparatus with the ejection rod 300 in the expulsion position. Sample 410 extracted from source material 380 is stored in sample sleeve 150 and ejected by ejection rod 300.

A preferred embodiment of this invention is the ergonomic design accomplished by the use of juxtaposed spur gears 310 and 330 in FIGS. 4, 5 and 6. This gear arrangement has allowed the device to be constructed such that it is ergonomically sculpted to be held in either hand, in a comfortable position with the hollow clamshell casing 100 resting in the palm of the hand with fingers positioned within the front contours 120 and under the horizontal extension 130 which rests over the forefinger, and thumb on an angular flat surface 210 at the top and to the rear. This handling arrangement is similar to the grip of a video game joystick or an Eppendorf® type pipetting device and is therefore familiar to the operator when holding the invention for the first time.

Still another preferred embodiment also arising from the spur gears 310 and 330 arrangement in FIGS. 4, 5 and 6 is the positioning of the actuation 160 and ejection 170 buttons which enables single hand use for both activation of the motor 240 and ejection of the sample 410 by depressing ejection button 170.

A preferred embodiment is the adoption of a motor 240 to rotate the sample sleeve 150. This eliminates the use of a manual coring tool that requires more time for the cut cycle and is an undesirable choice for a large number of samples. The use of a manual sampling tool in the past has resulted in related RSI injury due to lateral and vertical repeated movement of the wrist, required to operate the tool while collecting samples from source material 380. The motorized rotation of the sample sleeve 150 allows for high throughput sampling and continual use of the device without interruptions or stoppages. Consequently there is reduced strain to the technician's hand and wrist, which is common with the manual coring tool.

Another preferred embodiment is the plurality of different diameter collets 350 and ejection rod 300 diameters that match various sample cutting sleeve 150 sizes can be used.

Another preferred embodiment is the combined sharp cutting edge and rotational motion of the sample sleeve 150. This is consistent with that of the manual coring devices and eliminates cross contamination between samples. The cutting edge of the sample sleeve 150 combined with the rotational motion which does not shear the source material 380 when collecting a sample 410, and therefore does not tear the sample, as is common with conventional paper punching devices. Therefore no artefact fibers are created and there is no residue carried over between samples.

Another preferred embodiment is the variable length of the ejection rod 250 and sample sleeve 150 which can be accommodated in the apparatus, thereby allowing for the ejection of sample 410 into deep vials 420 or for extraction of sample 410 from hard to access source materials.

Another preferred embodiment is the location of the ejection shaft 250 down the center of the primary drive shaft 320 thereby allowing ejection rod 300 to fit inside of sample sleeve 150 for the ejection operation of the stored sample 410 from the sample sleeve 150. No other electric punching device operates with this combined coring, sample storage, and ejecting system.

Another preferred embodiment is the use of the compression spring 220 to bias the ejection shaft 250 in the retracted and stowed position. In high throughput situations, this operation can be completed rapidly, for quick release of sample 410. Alternatively the ejection may be slower for gradual release and careful positioning of sample 410 onto sample stages or slides, for example.

Another preferred embodiment arising from the motorized rotation of the sample sleeve 150 is that less downward force is required to be applied than is otherwise needed for the manual coring device to cut through the paper sample. The constant circular rotation cuts into the source material 380 with minimal downward pressure. The downward pressure required to excise a sample will vary depending on the physical properties of the source material.

Still another preferred embodiment arising from the motorized rotation is that the sample sleeve 150 is that the device allows for thicker source materials to be sampled without creation of artefact fibers. This increases the versatility of this sampling tool over manual tools which would necessitate increased downward pressure and increase the likelihood of RSI to the hand and wrist.

Still another preferred embodiment is the incorporation of a battery operated power supply with a recharging system for cordless use.

Still another preferred embodiment is the reduced number of moving parts and therefore reduce or eliminated the generation of static electricity, commonly associated with large, multi-component bench top punching systems. With little or no static and no artefact fiber, the potential for cross contamination between samples is virtually eliminated.

The present embodiments allow the entire sample to be ejected from tubular cutting sleeve 150 into a receptacle, i.e. vial 420 without manually working the sample 410 free from the sample sleeve 150. The sample 410 is cut and retrieved in a single, simultaneous step, without use of tweezers to lift sample 410 after extraction. The sample 410 can be ejected in a rapid or slow manner, depending on the specific demands of individual source materials.

As shown in FIG. 6 the sample taking device is comprised of a hollow clamshell casing 100, a sample sleeve 150, ejection shaft 250, motor 240. Motor 240 is used to rotate sample sleeve 150 to core a sample 410 from a substrate 380, which is held within the sample sleeve 150, which is ejected by ejection rod 300 which is pressure fit into the ejection shaft 250 when ejection button 170 is depressed.

The design of a sample taking device in FIG. 1 is such that the hollow clamshell casing 100 rests comfortably in the palm of either hand with the fingers resting on the contours 120 in front and under horizontal curved extension 130 with the thumb on a flat surface 210 at the top and to the rear. The base of the hand rests on a flange 110 at the base of the hollow clamshell casing. The wrist is maintained in a neutral, straight position and the hand grasps the hollow clamshell casing 100 to lift and lower the unit for cutting. No rotation of the hand or wrist is required for sample collection, therefore there is minimal repetitive stress in the wrist as is common with the prior art, manual coring devices.

I claim:

1. A motorized apparatus to collect a sample comprising:
  a hollow clamshell casing having a top portion, a bottom portion and a tubular handle portion connecting said top portion to said bottom portion;
  a sample collet system connected to said bottom portion of the casing adapted to receive a sample sleeve;
  said sample sleeve extending downward from the casing, a distal end of said sample sleeve forming a cutting edge circumscribing a circular cutting region;

an ejection rod being reciprocally slideable within said sample sleeve from a retracted position to an expulsion position past said cutting edge;

an electric gear motor disposed within the casing;

motor actuation means to drive a first and second spur gear disposed within the casing and thereby rotating said sample sleeve to collect a sample from a substrate when the cutting edge contacts said substrate;

ejection means to move said ejection rod from the retracted position to the expulsion position to displace said sample from the sample sleeve; and a collet locking mechanism disposed below said bottom portion of said casing, for removal of said sample collet system, or replacement of said sample sleeve and/or said ejection rod.

2. The apparatus of claim 1, wherein said handle portion comprises contours designed to accommodate a left or a right hand of a user.

3. The apparatus of claim 1, wherein said top portion of the casing further includes a horizontal projection extending from a side of the apparatus.

4. The apparatus of claim 3 comprising a flanged bottom portion of the casing.

5. The apparatus of claim 1, wherein said gear motor comprises an output shaft and a primary drive shaft wherein said first spur gear is attached to the output shaft and said second spur gear is attached to said primary drive shaft, said first spur gear is radially aligned and in meshing engagement with said second spur gear.

6. The apparatus of claim 5, wherein said sample collet system includes a collet nut that is threaded on to the primary drive shaft and compresses a collet which holds the sample sleeve.

7. The apparatus of claim 6, wherein said collet locking system comprises a spindle lock button biased in a first position, said spindle lock button when unbiased is moveable to a second position and engageable with said primary drive shaft thereby preventing rotation of said primary drive shaft for removal of the sample sleeve.

8. The apparatus of claim 5, wherein said ejection rod is pressure fit in an ejection shaft.

9. The apparatus of claim 8, wherein said ejection shaft is disposed within said primary drive, said ejection shaft connected to said ejection means.

10. The apparatus of claim 9 including biasing means to bias said ejection shaft and ejection rod in said retracted position.

11. The apparatus of claim 10, wherein said ejection means comprises an ejection button positioned on the top portion of the casing, biased in a first position by a compression spring.

12. The apparatus of claim 11, wherein said ejection button when unbiased in a second position causes the ejection shaft to extend and move said ejection rod from the retracted position to said expulsion position.

13. The apparatus of claim 5, wherein said motor actuation means comprises a button positioned on the top portion of the casing biased in an open position by a compression spring.

14. The apparatus of claim 13, wherein said motor actuation means, when unbiased in a closed position actuates said gear motor, thereby rotating the primary drive shaft to rotate said sample sleeve.

15. The apparatus of claim 1, wherein said ejection means is disposed adjacent to said motor actuation mean on the top portion of the casing.

* * * * *